(12) United States Patent
Hong et al.

(10) Patent No.: US 11,760,721 B2
(45) Date of Patent: Sep. 19, 2023

(54) POLYMERIZABLE COMPOSITION FOR POLYTHIOURETHANE-BASED OPTICAL MATERIAL

(71) Applicant: SKC CO., LTD., Gyeonggi-do (KR)

(72) Inventors: Seung Mo Hong, Incheon (KR); Jung Hwan Myung, Seoul (KR); Hyeon Myeong Seo, Ulsan (KR); Junghwan Shin, Gyeonggi-do (KR)

(73) Assignee: SKC CO., LTD., Gyeonggi-do (KR)

( * ) Notice: Subject to any disclaimer, the term of this patent is extended or adjusted under 35 U.S.C. 154(b) by 384 days.

(21) Appl. No.: 16/314,306

(22) PCT Filed: Jun. 26, 2017

(86) PCT No.: PCT/KR2017/006717
§ 371 (c)(1),
(2) Date: Dec. 28, 2018

(87) PCT Pub. No.: WO2018/004217
PCT Pub. Date: Jan. 4, 2018

(65) Prior Publication Data
US 2020/0290957 A1    Sep. 17, 2020

(30) Foreign Application Priority Data

Jun. 30, 2016 (KR) .......................... 10-2016-0082622

(51) Int. Cl.
| | | |
|---|---|---|
| *C08L 75/04* | (2006.01) | |
| *C07C 321/14* | (2006.01) | |
| *C08G 18/52* | (2006.01) | |
| *C08K 5/521* | (2006.01) | |
| *C08G 18/24* | (2006.01) | |
| *C08G 18/28* | (2006.01) | |
| *C08G 18/38* | (2006.01) | |
| *C08G 18/50* | (2006.01) | |
| *C08G 18/76* | (2006.01) | |
| *G02B 1/04* | (2006.01) | |

(52) U.S. Cl.
CPC .......... *C07C 321/14* (2013.01); *C08G 18/246* (2013.01); *C08G 18/281* (2013.01); *C08G 18/3876* (2013.01); *C08G 18/5072* (2013.01); *C08G 18/5084* (2013.01); *C08G 18/52* (2013.01); *C08G 18/7642* (2013.01); *C08K 5/521* (2013.01); *C08L 75/04* (2013.01); *G02B 1/041* (2013.01); *C08L 2201/08* (2013.01)

(58) Field of Classification Search
CPC ..... C07C 321/14; C08L 75/04; C08G 18/246; C08G 18/281; C08G 18/3876; C08G 18/5072; C08G 18/5084; C08G 18/52; C08G 18/7642; C08K 5/521

USPC .......................................................... 524/91
See application file for complete search history.

(56) References Cited

U.S. PATENT DOCUMENTS

| | | | | |
|---|---|---|---|---|
| 2008/0097045 | A1* | 4/2008 | Isahaya ................. | C08G 18/12 525/457 |
| 2008/0281034 | A1* | 11/2008 | Ganguli ............. | C08G 18/4063 524/539 |
| 2010/0063220 | A1 | 3/2010 | Van Der Ven et al. | |
| 2010/0298521 | A1* | 11/2010 | Kuma ................ | C08G 65/3348 528/85 |
| 2012/0315485 | A1* | 12/2012 | Iwazumi ............. | C09D 175/04 428/412 |

FOREIGN PATENT DOCUMENTS

| | | | |
|---|---|---|---|
| EP | 1950197 A1 | 7/2008 | |
| EP | 2980113 A1 * | 2/2016 | ....... B29D 11/00038 |
| JP | 03062817 A * | 3/1991 | ......... C08G 18/3876 |
| JP | H03-062817 A | 3/1991 | |
| JP | 10-319201 A | 12/1998 | |
| JP | 2003-322701 A | 11/2003 | |
| JP | 2005-336104 A | 12/2005 | |
| JP | 2006265402 | 10/2006 | |
| KR | 1020110034046 | 4/2011 | |
| KR | 1020120059634 | 6/2012 | |
| KR | 1020120100825 | 9/2012 | |
| KR | 1020120107889 | 10/2012 | |
| KR | 101205467 | 11/2012 | |
| KR | 101338568 | 12/2013 | |
| KR | 101533207 | 7/2015 | |
| WO | 2013/139602 A1 | 9/2013 | |
| WO | WO-2013139602 A1 * | 9/2013 | ......... C08G 18/3876 |
| WO | 2015/064548 A1 | 5/2015 | |
| WO | WO-2015163313 A1 * | 10/2015 | ....... B29D 11/00355 |

OTHER PUBLICATIONS

Office Action issued by the Korean Intellectual Property Office dated Jun. 14, 2017.
Office Action issued by the Japanese Patent Office dated Jan. 25, 2022.

* cited by examiner

*Primary Examiner* — Kelechi C Egwim
(74) *Attorney, Agent, or Firm* — IP & T GROUP LLP

(57) ABSTRACT

An embodiment relates to a polymeric composition for a polythiourethane-based optical material, wherein the polymeric composition, comprising a particular additive, may appropriately adjust the reactivity of an isocyanate such that viscosity is maintained low for a predetermined period of time, and thus is capable of preparing a high-quality polythiourethane-based optical material, without a complicated purification process. Moreover, a polythiourethane-based optical material according to an embodiment has not only a uniform refractive index, but also a low yellow index, and thus may be used as a variety of plastic optical lenses, such as an eyeglass lens or a camera lens and the like.

11 Claims, No Drawings

POLYMERIZABLE COMPOSITION FOR POLYTHIOURETHANE-BASED OPTICAL MATERIAL

This application is a national stage application of PCT/KR2017/006717 filed on Jun. 26, 2017, which claims priority of Korean patent application number 10-2016-0082622 filed on Jun. 30, 2016. The disclosure of each of the foregoing applications is incorporated herein by reference in its entirety.

TECHNICAL FIELD

The present embodiments relate to a polymeric composition for a polythiourethane-based optical material, and a polythiourethane-based optical material obtained to therefrom.

BACKGROUND ART

Plastic-based optical materials are light and have good dyeing properties and do not easily break as compared with optical materials composed of inorganic materials such as glass. Thus plastic materials of various resins are widely used as optical materials for eyeglass lenses and camera lenses and the like. Recently, as demand for higher performance and convenience increases, research on optical materials having such properties as high transparency, high refractive index, high Abbe number, low specific gravity, high heat resistance, high impact resistance, etc. continues.

An example of a widely used optical material is a polythiourethane compound obtained by polymerizing a polythiol-based compound and an isocyanate-based compound. However, when preparing a polythiourethane-based optical material by reacting a polythiol-based compound and an isocyanate-based compound, impurities, such as metal cation materials (for example, cations of Ca, Mg, K, Na, etc.) or nitrogen-containing compounds (for example, amine, etc.) and the like from the polythiol compounds, often increase reactivity of the isocyanate compounds, thereby inducing rapid curing to cause difficulties in the preparation of the target polythiourethane optical material. Moreover, as a result, the prepared optical material could show a partially non-uniform refractive index.

Accordingly, various efforts have been made to reduce impurity contents in polythiol or adjust the reactivity between a polythiol and an isocyanate.

For example, Korean Patent No. 10-1338568 discloses a method for preparing a polythiol compound by using a thiourea having a calcium content of at most 1.0 wt %. However, handling a thiourea is difficult, and there is a problem that the quality of the polythiol compound varies widely depending on a purification method.

Moreover, Korean Patent No. 10-1205467 discloses a method for adjusting the reactivity between a polythiol and an isocyanate by adjusting the pH of the polythiol to between 3.1 and 7. However, since a polythiol needs to be washed several times with acidic and basic aqueous solutions to adjust the pH of the polythiol, there are another problems of wastewater generation, reduced process yield, and degradation of optical properties of a polythiol, and the like.

Furthermore, Korean Patent No. 10-1533207 discloses a method for manufacturing a plastic lens by a using a polythiol in which the content of a nitrogen-containing compound is at most 3 wt %. However, the content of the nitrogen-containing compound varies even with the same method for preparing the polythiol, thereby leading to difficulties in quality control.

DISCLOSURE OF INVENTION

Technical Problem

Thus, an object of an embodiment is to provide a polymeric composition capable of preparing a high-quality polythiourethane-based optical material without a complicated purification process.

Solution to Problem

An embodiment provides a polymeric composition comprising (i) a polythiol compound; (ii) an isocyanate compound, and (iii) an acid component comprising a monovalent to tetravalent carboxylic acid, phosphoric acid, or a mixture thereof.

Another embodiment provides a polythiourethane-based compound obtained from the polymeric composition.

Still another embodiment provides an optical material molded from the polythiourethane-based compound.

Advantageous Effects of Invention

A polymeric composition according to an embodiment, comprising a particular additive, may appropriately adjust the reactivity of an isocyanate such that viscosity is maintained low for a predetermined period of time, and thus, is capable of preparing a high-quality polythiourethane-based optical material, without a complicated purification process. Moreover, a polythiourethane-based optical material has not only a uniform refractive index, but also a low yellow index, and thus may be used as a variety of plastic optical lenses, such as an eyeglass lens or a camera lens and the like.

BEST MODE FOR CARRYING OUT THE INVENTION

An embodiment provides a polymeric composition comprising (i) a polythiol compound; (ii) an isocyanate compound; and (iii) an acid component comprising a monovalent to tetravalent carboxylic acid, phosphoric acid, or a mixture thereof.

The acid component forms a salt with a metal cation material and a nitrogen-containing compound which are residual impurities in the polythiol compound, thereby appropriately adjusting the reactivity of the isocyanate to prevent rapid curing and induce stable polymerization of a polythiourethane-based compound.

The carboxylic acid may be one or more selected from the group consisting of monovalent saturated fatty acids such as methanoic acid, ethanoic acid, propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid (oleic acid), nonadecylic acid, icosanoic acid and the like; monovalent unsaturated fatty acids such as undecylenic acid, palmitoleic acid, oleic acid, linoleic acid, arachidonic acid, erucic acid and the like; dicarboxylic acids such as ethanedioic acid (oxalic acid), propanedioic acid, butanedioic acid, pentanedioic acid, hexanedioic acid, heptanedioic acid, octanedioic acid, nonanedioic acid, decanedioic acid, undecanedioic acid, dodecanedioic acid, hexadecanedioic acid, maleic acid, fumaric acid, glutaconic acid, traumatic acid, muconic acid, glutinic acid, citraconic acid, mesaconic acid, hydroxybutanedioic acid, 2-aminobutanedioic acid, 2-aminopentanedioic acid, 2-hydroxypropanedioic acid, 2,3-dihydroxybutanedioic acid, (2R,6S)-2,6-diaminoheptanedioic acid, (2S,3 S,4S,5R)-2,3,4,5-tetrahydroxyhexanedioic acid, oxopropanedioic acid, oxobutanedioic acid, 3-oxopentanedioic acid, 2,3,4-trihydroxypentanedioic acid and the like; aromatic dicarboxylic acids such as benzene-1,2-dicarboxylic acid, benzene-1,3-dicarboxylic acid, benzene-1,4-dicarboxylic acid, 2-(2-carboxyphenyl)benzoic acid, 2,6-naphthalenedicarboxylic acid and the like; tricarboxylic acids such as 2-hydroxypropane-1,2,3-tricarboxylic acid, 1-hydroxypropane-1,2,3-tricarboxylic acid, prop-1-ene-1,2,3-tricarboxylic acid, propane-1,2,3-tricarboxylic acid, benzene-1,3,5-tricarboxylic acid and the like; thioglycolic acid; 2-hydroxybutyric acid; thiolactic acid; 3-hydroxybutyric acid; 3-mercaptopropionic acid; and 4-hydroxybutyric acid. Specifically, the carboxylic acid may be one or more selected from the group consisting of oleic acid, oxalic acid, palmitoleic acid, linoleic acid, propanedioic acid, and butanedioic acid.

The acid component may be one or more selected from the group consisting of oleic acid, oxalic acid, palmitoleic acid, linoleic acid, propanedioic acid, butanedioic acid, and phosphoric acid.

The polymeric composition may comprise the acid component in an amount of 0.1 to 1 part by weight with respect to 100 parts by weight as the sum of the polythiol compound and the isocyanate compound. Specifically, the polymeric composition may comprise the acid component in an amount of 0.2 to 0.85 part by weight or 0.3 to 0.7 part by weight with respect to 100 parts by weight as the sum of the polythiol compound and the isocyanate compound.

The polymeric composition may comprise oleic acid, oxalic acid, or phosphoric acid in an amount of 0.1 to 1 part by weight with respect to 100 parts by weight as the sum of the polythiol compound and the isocyanate compound. Specifically, the polymeric composition may comprise oleic acid, oxalic acid, or phosphoric acid in an amount of 0.2 to 0.85 part by weight or 0.3 to 0.7 part by weight with respect to 100 parts by weight as the sum of the polythiol compound and the isocyanate compound.

The polythiol compound may be a typical one used in the synthesis of polythiourethane. Specifically, the polythiol compound may comprise one or more selected from the group consisting of bis(2-(2-mercaptoethylthio)-3-mercaptopropyl)sulfide, 4-mercaptomethyl-1,8-dimercapto-3,6-dithiaoctane, 2,3-bis(2-mercaptoethylthio)propane-1-thiol, 2,2-bis(mercaptomethyl)-1,3-propanedithiol, bis(2-mercaptoethyl)sulfide, tetrakis(mercaptomethyl)methane, 2-(2-mercaptoethylthio)propane-1,3-dithiol, 2-(2,3-bis(2-mercaptoethylthio)propylthio)ethanethiol, bis(2,3-dimercaptopropanyl)sulfide, bis(2,3-dimercaptopropanyl)disulfide, 1,2-bis(2-mercaptoethylthio)-3-mercaptopropane, 1,2-bis(2-(2-mercaptoethylthio)-3-mercaptopropylthio)ethane, 2-(2-mercaptoethylthio)-3-2-mercapto-3-[3-mercapto-2-(2-mercaptoethylthio)-propylthio]propylthio-propane-1-thiol, 2,2-bis-(3-mercapto-propionyloxymethyl)-butyl ester, 2-(2-mercaptoethylthio)-3-(2-(2-[3-mercapto-2-(2-mercaptoethylthio)-propylthio]ethylthio)ethylthio)propane-1-thiol, (4R,11 S)-4,11-bis(mercaptomethyl)-3,6,9,12-tetrathiatetradecane-1,14-dithiol, (S)-3-((R-2,3-dimercaptopropyl)thio)propane-1,2-dithiol, (4R,14R)-4,14-bis(mercaptomethyl)-3,6,9,12,15-pentathiaheptane-1,17-dithiol, (S)-3-((R-3-mercapto-2-((2-mercaptoethyl)thio)propyl)thio)propyl)thio)-2-((2-mercaptoethyl)thio)propane-1-thiol, 3,3'-dithiobis(propane-1,2-dithiol), (7R,11 S)-7,11-bis(mercaptomethyl)-3,6,9,12,15-pentathiaheptadecane-1,17-dithiol, (7R,12S)-7,12-bis(mercaptomethyl)-3,6,9,10,13,16-hexathiaoctadecane-1,18-dithiol, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, pentaerythritol tetrakis(3-mercaptopropionate), trimethylolpropane tris(3-mercaptopropionate), pentaerythritol tetrakis(2-mercaptoacetate), bispentaerythritol-ether-hexakis (3-mercaptopropionate), 1,1,3,3-tetrakis(mercaptomethylthio)propane, 1,1,2,2-tetrakis(mercaptomethylthio)ethane, 4,6-bis(mercaptomethylthio)-1,3-dithiane, and 2-(2,2-bis(mercaptodimethylthio)ethyl)-1,3-dithiane.

The polythiol compound may comprise a metal cation impurity, a nitrogen-containing impurity, or a mixture thereof.

The polythiol compound may comprise 100 to 6,000 ppm of the metal cation impurity. Specifically, the polythiol compound may comprise 500 to 5,000 ppm of the metal cation impurity. Moreover, the metal cation impurity may be one or more selected from the group consisting of Ca cations, Mg cations, K cations, and Na cations.

The polythiol compound may comprise 3 to 10 wt % of the nitrogen-containing impurity based on the total weight of the polythiol compound. Specifically, the polythiol compound may comprise 5 to 8 wt % of the nitrogen-containing impurity based on the total weight of the polythiol compound. Moreover, the nitrogen-containing impurity may be one or more selected from melamines, ureas, triazines, amides, imides, or imines.

The isocyanate compound may be one typically used in the synthesis of polythiourethane. Specifically, the isocyanate compound may comprise one or more selected from the group consisting of aliphatic isocyanate compounds such as isophoronediisocyanate, dicyclohexylmethane-4,4-diisocyanate, hexamethylenediisocyanate, 2,2-dimethylpentanediisocyanate, 2,2,4-trimethylhexanediisocyanate, butenediisocyanate, 1,3-butadiene-1,4-diisocyanate, 2,4,4-trimethylhexamethylenediisocyanate, 1,6,11-undecatriisocyanate, 1,3,6-hexamethylenetriisocyanate, 1,8-diisocyanate-4-isocyanatomethyloctane, bis(isocyanatoethyl)carbonate, bis(isocyanatoethyl)ether and the like; cycloaliphatic isocyanate compounds such as isophoronediisocyanate, 1,2-bis(isocyanatomethyl)cyclohexane, 1,3-bis(isocyanatomethyl)cyclohexane, 1,4-bis(isocyanatomethyl)cyclohexane, dicyclohexylmethanediisocyanate, cyclohexanediisocyanate, methylcyclohexanediisocyanate, dicyclohexyldimethylmethaneisocyanate, 2,2-dimethyldicyclohexylmethaneisocyanate and the like; aromatic isocyanate compounds such as bis(isocyanatoethyl)benzene, bis(isocyanatopropyl)benzene, bis(isocyanatobutyl)benzene, bis(isocyanatomethyl)naphthalene, bis(isocyanatomethyl)diphenylether, phenylenediisocyanate, ethylphenylenediisocyanate, isopropylphenylenediisocyanate, dimethylphenylenediisocyanate, diethylphenylenediisocyanate, diisopropylphenylenediisocyanate, trimethylbenzenetriisocyanate, benzenetriisocyanate, biphenyldiisocyanate, toluidinediisocyanate, 4,4-diphenylmethanediisocyanate, 3,3-dimethyldiphenylmethane-4,4-diisocyanate, bibenzyl-4,4-diisocyanate, bis(isocyanatophenyl)ethylene, 3,3-di methoxybiphenyl-4,4-diisocyanate, hexahydrobenzenediisocyanate, hexahydrodiphenylmethane-4,4-diisocyanate, o-xylenediisocyanate, m-xylenediisocyanate, p-xylenediisocyanate and the like; sulfur-containing aliphatic isocyanate compounds such as bis(isocyanatoethyl)sulfide, bis(isocyanatopropyl)

sulfide, bis(isocyanatohexyl)sulfide, bis(isocyanatomethyl)sulfone, bis(isocyanatomethyl)disulfide, bis(isocyanatopropyl)disulfide, bis(isocyanatomethylthio)methane, bis(isocyanatoethylthio)methane, bis(isocyanatoethylthio)ethane, bis(isocyanatomethylthio)ethane, 1,5-diisocyanato-2-isocyanatomethyl-3-thiapentane and the like; sulfur-containing aromatic isocyanate compounds such as diphenylsulfide-2,4-diisocyanate, diphenylsulfide-4,4-diisocyanate, 3,3-dimethoxy-4,4-diisocyanatodibenzylthioether, bis(4-isocyanatomethylbenzene)sulfide, 4,4-methoxybenzenethioethyleneglycol-3,3-diisocyanate, diphenyldisulfide-4,4-diisocyanate, 2,2-dimethyldiphenyldisulfide-5,5-diisocyanate, 3,3-dimethyldiphenyldisulfide-5,5-diisocyanate, 3,3-dimethyldiphenyldisulfide-6,6-diisocyanate, 4,4-dimethyldiphenyldisulfide-5,5-diisocyanate, 3,3-dimethoxydiphenyldisulfide-4,4-diisocyanate, 4,4-dimethoxydiphenyldisulfide-3,3-diisocyanate and the like; and sulfur-containing heterocyclic isocyanate compounds such as 2,5-diisocyanatothiophene, 2,5-bis(isocyanatomethyl)thiophene, 2,5-diisocyanatotetrahydrothiophene, 2,5-bis(isocyanatomethyl)tetrahydrothiophene, 3,4-bis(isocyanatomethyl)tetrahydrothiophene, 2,5-diisocyanato-1,4-dithiane, 2,5-bis(isocyanatomethyl)-1,4-dithiane, 4,5-diisocyanato-1,3-dithiolane, 4,5-bis(isocyanatomethyl)-1,3-dithiolane, 4,5-bis(isocyanatomethyl)-2-methyl-1,3-dithiolane and the like.

The polymeric composition may comprise a polythiol compound and an isocyanate compound in an equivalent ratio of 0.5 to 1.5:1. Specifically, the polymeric composition may comprise the polythiol compound and the isocyanate compound in an equivalent ratio of 0.8 to 1.2:1.

The acid component may be premixed with the polythiol compound or with the isocyanate compound, as needed.

The polymeric composition may exhibit a viscosity (25° C.) of 1,000 cPs (centipoise) or less after being placed at 25° C. for 8 hours. Specifically, the polymeric composition may exhibit a viscosity (25° C.) of 700 cPs or less, or a viscosity (25° C.) of 200 to 700 cPs, after being placed at 25° C. for 8 hours.

A polymeric composition according to another embodiment may further comprise an additive, such as an internal release agent, a reaction catalyst, a heat stabilizer, a UV absorber, or a bluing agent and the like, depending on the objective.

A benzophenone, benzotriazole, salicylate, cyanoacrylate, or oxanilide-based compounds and the like may be used as the UV absorber. Moreover, the internal release agent may be selected from fluorine-based nonionic surfactants having a perfluoroalkyl group, a hydroxyalkyl group, or a phosphate ester group; silicone-based nonionic surfactants having a dimethylpolysiloxane group, a hydroxyalkyl group, or a phosphate ester group; alkyl-based quaternary ammonium salts such as trimethylcetyl ammonium salt, trimethylstearyl, dimethylethylcetyl ammonium salt, triethyldodecyl ammonium salt, trioctylmethyl ammonium salt, or diethylcyclohexadodecyl ammonium salt and the like; and acidic phosphate esters, and may be used alone, or as a combination of two or more thereof.

The reaction catalyst may be a known reaction catalyst that can be used in the preparation of polythiourethane-based compounds. Specifically, dialkyltin halides such as dibutyltin dichloride, dimethyltin dichloride and the like; dialkyltin dicarboxylates such as dimethyltin diacetate, dibutyltin dioctanoate, dibutyltin dilaurate and the like; dialkyltin dialkoxides such as dibutyltin dibutoxide, dioctyltin dibutoxide and the like; dialkyltin dithioalkoxides such as dibutyltin di(thiobutoxide) and the like; dialkyltin oxides such as di(2-ethylhexyl)tin oxide, dioctyltin oxide, bis(butoxydibutyltin)oxide and the like; and dialkyltin sulfides such as dibutyltin sulfide and the like may be used as the reaction catalyst. More specifically, dialkyltin halides such as dibutyltin dichloride, dimethyltin dichloride and the like may be used as the reaction catalyst.

The bluing agent has an absorption band in the orange to yellow wavelength range of the visible light range, and has a function of adjusting the color of an optical material composed of a resin. Specifically, the bluing agent may comprise materials that exhibit colors from blue to purple, but is not limited thereto. Moreover, the bluing agent may be a dye, a fluorescence brightening agent, a fluorescent pigment, inorganic pigment and the like, and may be appropriately selected in accordance with the physical properties or resin color and the like required by a final optical product. Each of the bluing agents may be used alone, or as a combination of two or more thereof. In terms of solubility in a polymeric composition and transparency of the optical material, the bluing agent is desirably a dye. In terms of absorption wavelength, the dye may have a maximum absorption wavelength of 520 to 600 nm, and more particularly, have a maximum absorption wavelength of 540 to 580 nm. Moreover, in terms of the structure of a compound, the dye is desirably an anthraquinone dye. Methods for adding the bluing agent are not particularly limited, and the bluing agent may be pre-added to a monomer system. Specifically, various methods may be used for adding the bluing agent, such as a method in which the bluing agent is dissolved in a monomer, or a method in which a master solution containing a high concentration of the bluing agent is prepared and then diluted with a monomer to be used or other additive.

Another embodiment provides a polythiourethane-based compound obtained from such a polymeric composition as described above.

The polythiourethane-based compound is prepared through polymerization (and curing) of a polythiol compound and an isocyanate compound. As described above, during the polymerization, an acid component added to the polymeric composition forms salts with impurities present in the polythiol compound to appropriately adjust the reactivity of the isocyanate compound, thereby facilitating efficient synthesis of the polythiourethane-based compound.

In the polymerization reaction, the reaction mole ratio of SH groups/NCO groups may be 0.5 to 3.0, and may particularly be 0.8 to 1.3.

Moreover, in order to adjust the reaction rate, a reaction catalyst typically used in polythiourethane preparation may be added. A tin-based catalyst may be used as the reaction catalyst, and, for example, dibutyltin dichloride, dibutyltin dilaurate, dimethyltin dichloride and the like may be used.

Another embodiment provides an optical material molded from such a polythiourethane-based compound as described above.

That is, the optical material may be prepared by polymerizing and molding a polymeric composition (comprising a polythiol compound, an isocyanate compound and an acid component).

First, after being degassed under reduced pressure, the polymeric composition is injected into a mold for molding an optical material. Such degassing and mold injection may be performed at a temperature range of 20 to 40° C. After the injection into the mold, polymerization is typically performed by gradual heating from a low temperature to a high temperature.

The temperature of the polymerization reaction may be 30 to 150° C., and more specifically, may be 40 to 130° C.

Moreover, in order to adjust the reaction rate, a reaction catalyst typically used in the preparation of polythiourethane may be added, examples of which have been provided above.

Afterwards, a polythiourethane-based optical material is separated from the mold.

The optical material may be prepared in various shapes by changing the mold to be used. Specifically, the optical material may be in the form of an eyeglass lens, a camera lens, or a light-emitting diode (LED) and the like.

When the color coordinates of the optical material are measured, the optical material may have a yellow index of 6 or less. The lower the yellow index, the better the color of the optical material, and the higher the yellow index, the poorer the color. The yellow index value is obtained by measuring a circular optical material having an average thickness of 9 mm and an average diameter of 75 mm, and may be a value calculated by applying chromaticity coordinates x and y—measured using a Minolta CM-5 color difference meter—to Mathematical Formula 1 below.

Yellow index=$(234x+106y+106)/y$ [Mathematical Formula 1]

The optical material may desirably be an optical lens, particularly a plastic optical lens.

As such, a polymeric composition according to an embodiment, by comprising a particular additive, may appropriately adjust the reactivity of isocyanate such that viscosity is maintained low for a predetermined period of time, and thus, is capable of preparing a high-quality polythiourethane-based optical material, even without a complicated purification process. Moreover, a polythiourethane-based optical material according to another embodiment has not only a uniform refractive index, but also a low yellow index, and thus may be used as a variety of plastic lenses, such as an eyeglass lens or a camera lens and the like.

MODE FOR THE INVENTION

Hereinafter, the embodiments are explained in detail by Examples. The following Examples are intended to further illustrate the embodiments without limiting its scope.

Example 1

A polymeric composition was prepared by mixing 50.7 parts by weight of m-xylenediisocyanate, 0.01 part by weight of dibutyltin dichloride as a curing catalyst, 0.1 part by weight of an internal release agent (manufacturer: Stepan, product name: Zelec® UN, acidic alkyl phosphate ester), 0.05 part by weight of a UV absorber (2-(2'-hydroxy-5'-t-octylphenyl)-2H-benzotriazole, manufacturer: Cytec, product name: CYASORB®UV-5411), and 0.5 part by weight of phosphoric acid at 25° C. to obtain a mixture, and adding 49.3 part by weight of polythiol B to the mixture and then mixing them again uniformly.

The polythiol B is bis(2-(2-mercaptoethylthio)-3-mercaptopropyl)sulfide represented by Formula 1 below, and HPLC measurement under the following measurement conditions revealed a high content of a nitrogen-containing compound, with the peak area of the nitrogen-containing compound (B)/the peak area of the polythiol compound (A) being 7.8%.

Moreover, inductively coupled plasma (ICP) analysis results of the polythiol B revealed that the polythiol B comprises 1.4 ppm of Ca, 1.6 ppm of Mg, 1.9 ppm of K, and 2.1 ppm of Na.

[Formula 1]

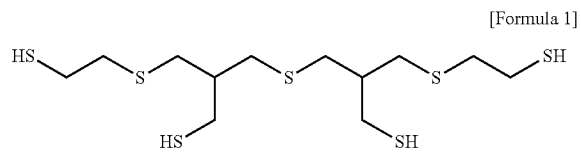 [SMILES: SCCSCC(CS)CSCC(CS)CSCCS]

<HPLC Measurement Conditions>
Column: YMC-Pack ODS-A A-312 (S5, diameter 6 mm×height 150 mm)
Mobile phase: acetonitrile/0.01 mol potassium dihydrogen phosphate aqueous solution=60/40 (v/v)
Flow rate: 1.0 mL/min
Detector: UV detector, wavelength 230 nm
Preparation of measurement solution: dissolve and mix in 160 mg of specimen in 10 mL of acetonitrile
Injection amount of measurement solution: 2 μL.

Examples 2 to 4 and Comparative Examples 1 to 3

Other than using components and contents (parts by weight) as indicated in Table 1 below, polymeric compositions were prepared using the same method as Example 1.

TABLE 1

| | | Example 1 | Example 2 | Example 3 | Example 4 | Comparative Example 1 | Comparative Example 2 | Comparative Example 3 |
|---|---|---|---|---|---|---|---|---|
| Isocyanate | | 50.7 | 50.7 | 50.7 | 50.7 | 50.7 | 50.7 | 50.7 |
| Curing catalyst | | 0.01 | 0.01 | 0.01 | 0.01 | 0.01 | 0.01 | 0.01 |
| Internal release agent | | 0.1 | 0.1 | 0.1 | 0.1 | 0.1 | 0.1 | 0.1 |
| UV absorber | | 0.05 | 0.05 | 0.05 | 0.05 | 0.05 | 0.05 | 0.05 |
| Acid component | Phosphoric acid | 0.7 | — | — | — | — | — | — |
| | Oleic acid | — | 0.7 | — | — | — | — | — |
| | Oxalic acid | — | — | 0.3 | 0.3 | — | — | — |
| Polythiol | Polythiol A | — | — | 49.3 | 49.3 | — | — | 49.3 |
| | Polythiol B | 49.3 | — | — | — | 49.3 | — | — |
| | Polythiol C | — | 49.3 | — | — | — | 49.3 | — |
| Additional impurities | Sodium carbonate | — | — | 0.5 | — | — | — | 0.5 |
| | Calcium chloride | — | — | — | 0.5 | — | — | — |

The polythiol A is bis(2-(2-mercaptoethylthio)-3-mercaptopropyl)sulfide represented by Formula 1 above, and HPLC measurement under the same conditions as Example 1 revealed a B/A percentage of 1.9%. Moreover, ICP analysis revealed that polythiol A comprises 1.0 ppm of Ca, 1.1 ppm of Mg, 1.2 ppm of K, and 1.7 ppm of Na.

The polythiol C is bis(2-(2-mercaptoethylthio)-3-mercaptopropyl)sulfide represented by Formula 1 above, and HPLC measurement under the same measurement conditions as Example 1 revealed a B/A percentage of 2.8%. Moreover, ICP analysis revealed that polythiol C comprises 1.3 ppm of Ca, 1.7 ppm of Mg, 1.8 ppm of K, and 621 ppm of Na, a high Na cation content.

Experimental Example: Measurement of Physical Properties

Physical properties of the polymeric compositions prepared in Examples 1 to 4 and Comparative Examples 1 to 3 were measured as described below, and the measurement results are shown in Table 2 below.

(1) Viscosity

Viscosity was measured using a rotational viscometer at 25° C. after placing the polymeric composition at 25° C. for 8 hours.

(2) Yellow Index and Light Resistance (ΔYI)

The polymeric compositions prepared in Examples 1 to 4 and Comparative Examples 1 to 3 were degassed for 1 hour at 600 Pa, and then filtered in a 3 μm Teflon filter. The filtered polymeric composition was injected into a glass mold assembled by tape. The temperature of the mold was increased from 25° C. to 120° C. at a rate of 5° C./minute, and polymerization was performed for 18 hours at 120° C. A resin cured in the glass mold was further cured for 4 hours at 130° C., and then a molded body was released from the mold.

The molded body was a circular lens (optical material) having a thickness of 9 mm and a diameter of 75 mm, the yellow index (YI) of the optical material was calculated by applying the chromaticity coordinates x and y measured by a Minolta CM-5 color difference meter to Mathematical Formula 1 below.

Yellow index=$(234x+106y+106)/y$  [Mathematical Formula 1]

After exposure of the optical material for 200 hours to a Q-Panel Lad Products QUV/Spray Model (5w), the yellow index thereof was measured using the same method described above. Afterwards, the difference in the yellow index value before and after exposure was shown as the light resistance (ΔYI).

As seen in Table 2, when comparing the polymeric compositions of Examples 1 to 4 with those of Comparative Examples 1 to 3, the viscosity of the polymeric compositions of Examples 1 to 4 was maintained low for a relatively long period of time, and lenses as molded from the polymeric compositions exhibited low yellow indices and excellent light resistance (ΔYI), and thus it could be seen that the polymeric compositions of Examples 1 to 4 were more appropriate as optical materials. In particular, direct comparisons could be made between polymeric compositions that used the same polythiol (same impurities content), that is, between Example 1 and Comparative Example 1, Example 2 and Comparative Example 2, and Example 3 and Comparative Example 3.

The invention claimed is:

1. A polymeric composition for a polythiourethane-based optical material, the polymeric composition comprising:
   (i) a polythiol compound;
   (ii) an isocyanate compound;
   (iii) an acid component comprising phosphoric acid; and
   (iv) a tin-based catalyst,
   wherein the polymeric composition comprises the acid component in an amount of 0.1 to 1 part by weight with respect to 100 parts by weight as the sum of the polythiol compound and the isocyanate compound,
   wherein the polymeric composition comprises an internal release agent, and
   wherein the internal release agent is one or more selected from the group consisting of fluorine-based nonionic surfactants having a perfluoroalkyl group, a hydroxyalkyl group, or a phosphate ester group; silicone-based nonionic surfactants having a dimethylpolysiloxane group, a hydroxyalkyl group, or a phosphate ester group; alkyl-based quaternary ammonium salts; and acidic phosphate esters.

2. The polymeric composition of claim 1, wherein the polymeric composition exhibits a viscosity (25° C.) of 1,000 cPs or less after being placed at 25° C. for 8 hours.

3. The polymeric composition of claim 1, wherein the polythiol compound comprises a metal cation impurity, a nitrogen-containing impurity, or a mixture thereof.

4. The polymeric composition of claim 3, wherein the polythiol compound comprises 100 to 6,000 ppm of the metal cation impurity.

5. The polymeric composition of claim 3, wherein the metal cation impurity is one or more selected from the group consisting of Ca cations, Mg cations, K cations, and Na cations.

6. The polymeric composition of claim 3, wherein the polythiol compound comprises 3 to 10 wt % of a nitrogen-containing impurity based on the total weight of the polythiol compound.

TABLE 2

|  | Example 1 | Example 2 | Example 3 | Example 4 | Comparative Example 1 | Comparative Example 2 | Comparative Example 3 |
|---|---|---|---|---|---|---|---|
| Viscosity (cPs) | 320 | 227 | 667 | 479 | 5,970 | 12,380 | not available (gelated) |
| Yellow index | 4.12 | 4.21 | 4.84 | 4.67 | 6.11 | 6.87 | 6.99 |
| Light resistance (ΔYI) | 1.11 | 1.09 | 1.19 | 1.27 | 2.66 | 2.59 | 2.91 |

7. The polymeric composition of claim 3, wherein the nitrogen-containing impurity is one or more selected from the group consisting of melamines, ureas, triazines, amides, imides, and imines.

8. A polythiourethane-based compound obtained from the polymeric composition of claim 1.

9. An optical material molded from the polythiourethane-based compound of claim 8.

10. The optical material of claim 9, wherein the optical material is a plastic optical lens.

11. The optical material of claim 9, wherein the optical material, when measured for chromaticity coordinates, has a yellow index of 6 or less.

* * * * *